(12) United States Patent
Bahmani et al.

(10) Patent No.: US 11,446,514 B2
(45) Date of Patent: Sep. 20, 2022

(54) SYSTEM AND METHOD TO STIMULATE THE OPTIC NERVE

(71) Applicant: Dopavision GmbH, Berlin (DE)

(72) Inventors: Hamed Bahmani, Berlin (DE); Christain Lautner, Berlin (DE); Markus Müschenich, Berlin (DE)

(73) Assignee: DOPAVISION GMBH, Berlin (DE)

( * ) Notice: Subject to any disclaimer, the term of this patent is extended or adjusted under 35 U.S.C. 154(b) by 0 days.

(21) Appl. No.: 16/703,997

(22) Filed: Dec. 5, 2019

(65) Prior Publication Data

US 2020/0108272 A1 Apr. 9, 2020

Related U.S. Application Data

(63) Continuation-in-part of application No. PCT/EP2018/065213, filed on Jun. 8, 2018.

(30) Foreign Application Priority Data

Jun. 8, 2017 (DE) ..................... 10 2017 112 694.5
Jun. 8, 2017 (LU) ....................................... 100280

(51) Int. Cl.
*A61N 5/06* (2006.01)
*A61N 5/067* (2006.01)

(52) U.S. Cl.
CPC ............ *A61N 5/0622* (2013.01); *A61N 5/067* (2021.08); *A61N 2005/0648* (2013.01); *A61N 2005/0652* (2013.01); *A61N 2005/0663* (2013.01)

(58) Field of Classification Search
CPC .......... A61N 5/0622; A61N 2005/0648; A61N 2005/067; A61N 2005/0658; A61N 5/0618; A61N 2005/0652; A61F 2009/00863
See application file for complete search history.

(56) References Cited

U.S. PATENT DOCUMENTS

| | | |
|---|---|---|
| 5,923,398 A | 7/1999 | Goldman |
| 2004/0070729 A1 | 4/2004 | Wiebe et al. |
| 2007/0018292 A1 | 1/2007 | Sutardja |
| 2007/0182928 A1* | 8/2007 | Sabel ........................ A61H 5/00 351/224 |

(Continued)

FOREIGN PATENT DOCUMENTS

| | | |
|---|---|---|
| CN | 1432348 A | 7/2003 |
| JP | 2016529965 A | 9/2016 |

(Continued)

OTHER PUBLICATIONS

"Kessel et al., Sleep Disturbances are Related to Decreased Transmission of Blue Light to the Retina Caused by Lens Yellowing, 2011, Glostrup Hospital, vol. 34, No. 9" (Year: 2011).*

(Continued)

*Primary Examiner* — Carl H Layno
*Assistant Examiner* — Aya Ziad Bakkar
(74) *Attorney, Agent, or Firm* — Pharma Patents International AG; Lily Ackerman

(57) ABSTRACT

A method for application of light to one or more eyes (300) of a user is disclosed. The method comprises identification (110) of location of an optic disk (330) on a retina (320) in the one or more eyes (300) and selectively applying (115) the light onto the optic disc (330) to stimulate the optic disk (330).

20 Claims, 3 Drawing Sheets

(56) References Cited

U.S. PATENT DOCUMENTS

| | | |
|---|---|---|
| 2007/0225775 A1 | 9/2007 | Tano et al. |
| 2014/0228824 A1* | 8/2014 | Yee ............... A61F 9/00821 606/4 |
| 2015/0142086 A1* | 5/2015 | Narita ............ A61N 5/0622 607/92 |
| 2016/0067086 A1 | 3/2016 | Tedford et al. |
| 2016/0270656 A1* | 9/2016 | Samec ............ G02B 21/0032 |

FOREIGN PATENT DOCUMENTS

| | | |
|---|---|---|
| WO | 2010/076706 A1 | 7/2010 |
| WO | 2014/172641 A1 | 10/2014 |
| WO | 2015010920 A1 | 1/2015 |
| WO | 2016/145064 A1 | 9/2016 |
| WO | 2016/162554 A1 | 10/2016 |

OTHER PUBLICATIONS

Dijk & Archer, "Light, Sleep, and Circadian Rhythms: Together Again", PLOS Biology, vol. 7, issue 6, e1000145, Jun. 2009.
Miyamoto, Murakami—2015—Pupillary light reflex to light inside the natural blind spot.
Mure et al.—2009—Melanopsin bistability A fly's eye technology in the human retina.
Phillips, Backhouse, Collins—2011—Myopia, Light and Circadian Rhythms.
Schaeffel, Smith—2017—Inhibiting Myopia by (Nearly) Invisible Light.
Torii, et al.—2016—Violet Light Exposure Can Be a Preventive Strategy Against Myopia Progression.
Xue et al.—2011—Melanopsin signalling in mammalian iris and retina.
Chinese Optical Technology Magazine, vol. 6, pp. 95-96, 2017.

* cited by examiner

SYSTEM AND METHOD TO STIMULATE THE OPTIC NERVE

CROSS REFERENCE TO RELATED APPLICATIONS

This application is a continuation-in-part of International Patent Application No. PCT/EP2018/065213 filed on 8 Jun. 2018, which claims benefit of and priority to Luxembourg Patent Application No. 100280 and German Patent Application No. 10 2017 112 694.5, both of which were filed on 8 Jun. 2017. The disclosures of each of these applications are hereby incorporated herein by reference in their entirety.

BACKGROUND OF THE INVENTION

Field of the Invention

The invention relates to a system and method to stimulate the optic nerve.

Brief Description of the Related Art

The 24-hour light-dark (LD) cycle is a fundamental characteristic of the Earth's environment and so the influence of this LD cycle on behavior and physiology of animals and humans is not surprising. Most biochemical, physiological and behavioral variables in humans fluctuate on such a rhythmic basis, and this is termed the "circadian rhythm". This circadian timing system enables a body to predict the onset of dawn and dusk and adjust physiological and behavioral systems of the body accordingly. It is now established that these daily rhythms are temporally organized by a circadian clock which maintains temporal synchronization between the body and the external environment, as well as the internal coordination of diverse physiological processes over time.

The LD cycle is the primary environmental agent that synchronizes the circadian clock of the body. The ability of the natural LD cycle to entrain the circadian rhythm is based on the response of the circadian clock to light.

Our eyes are the most common input for such light-dark time cue signals for synchronizing the LD cycle with the body's circadian rhythm. Light received by a retina in further processed by a brain to synchronize the circadian rhythm. In mammals, a tract of nerves, referred to as the retinohypothalamic tract (RHT), carry information about the light-dark environment directly from the retina to the suprachiasmatic nuclei (SCN). The SCN are a cluster of cells in the hypothalamus which receives the transduced light-dark time cue signals, indicating the transition from light to dark, via the RHT from the retinal ganglion cells (RGCs), and distributes the light-dark time cue signals via endocrine and neural pathways to various systems of the body to ensure the various systems are kept synchronous with day and night. When these pathways are disrupted, the rest-activity cycle of the body fails to be synchronized to the LD cycle.

It is known that off-phase light cues may interrupt the normal circadian rhythm. For example, exposure to light late in the biological day, around dusk, will delay the onset of activity in a nocturnal animal, and delay the onset of inactivity in a diurnal animal. Light exposure early in the biological day (dawn) will advance the onset of activity in a diurnal species, and advance the onset of sleep in a nocturnal species. This phase-shifting effect of light is clearly anon-image forming effect of light, which depends on circadian phase and plays an important role in the temporal organization of behavior in animals, including humans (Dijk & Archer, "Light, Sleep, and Circadian Rhythms: Together Again", PLOS Biology, vol. 7, issue 6, e1000145, June 2009).

Many physiological functions of the body are affected when the light arriving to the eye is off-phase, or undesired artificial light breaks the natural LD cycle. Light therapy has been shown to be effective for re-tuning the LD cycle in such cases. Light therapy (also called phototherapy) consists of exposure to light, daylight, or artificial light, with a specific spectrum and/or with a specific light radiance, for a prescribed amount of time and, in some cases, at a specific time of day.

Originally, scientists held a tacit belief that the light effects on the circadian rhythms, as well as other non-image forming effects, were mediated by the classical photoreceptors that mediate vision. This view was shattered when non-image forming responses were demonstrated in mice devoid of the then known photoreceptors: light still elicited circadian phase-shifting responses and the hormone melatonin was suppressed. Melatonin is the principal hormone of the pineal gland, and mediates many biological functions, particularly the timing of those physiological functions that are controlled by the duration of light and darkness. Light-induced suppression of melatonin had previously been shown to persist in some visually blind people. These data, as well as the demonstration that the spectral sensitivity of non-image forming responses differed from visual responses also in humans, were consistent with the existence of a novel photoreceptive system, subsequently identified as melanopsin.

The photopigment melanopsin is expressed in the inner retina of humans and other animals, and in particular in a subclass of ganglion cells, called intrinsically photosensitive retinal ganglion cells (ipRGCs). Melanopsin is most sensitive to blue light, but is also sensitive to other wavelengths of light in the visible spectrum. This non-visual photoresponse is essential for circadian entrainment in many non-visual functions. These non-visual functions include sleep/wake state (melatonin synthesis), pupil light reflex, cognitive performance, mood, locomotor activity, memory, body temperature, etc. ipRGCs indirect input via the SCN regulates the light-sensitive suppression of melatonin production in the pineal. In mice lacking the gene Opn4, which codes for melanopsin, phase shifts, pupillary constriction, and acute suppression of activity in response to light are all attenuated. Abolition of rods and cones, as well as the Opn4 gene, abolishes all known image forming and non-image forming effects, demonstrating that both the classical and novel photoreceptive system contribute to these responses.

The human eye can see wavelengths within a range of about 380 nm to about 780 nm. Within this visible light spectrum, some wavelengths can induce acute or cumulative photo damage to the eye, while other wavelengths are necessary to synchronize human biological rhythms. Historically light treatments have been applied through the eye via ambient light and/or dedicated task light. Providing therapy through conventional lighting systems would not separate or distinguish between the visual effect of the provided light (e.g. the image forming function of light) and the non-visual effect of the provided light (e.g. non-image forming functions controlling circadian rhythms), as all the light produced would be perceived by the eyes.

A number of patent documents are known that discuss the use of light treatment and apparatus used for this treatment. For example, International Patent Application No. WO 2016/162554 A1 discloses a head-mounted display device which emits light to the eye through a waveguide which is claimed to be helpful in treating light-related disorders. The display device has a controller module which adjusts the wavelength of the light emitted to the eye according to the optimally effective wavelength for ipRGCs. The device, however, does not include a method to distinguish between the non-image forming receptors and image-forming light receptors in the eye.

International Patent Application No. WO 2010/076706 A1 teaches a more specific approach to deliver light therapy to subjects, but the method of this disclosure is limited to special timeframes in a LD cycle i.e. during sleep or shortly before going to sleep etc. Therefore, the disclosed embodiment takes a form of sleep mask.

International Patent Application No. WO 2014/172641 (Index Corporation) teaches the delivery during retinal surgery of a series of short duration light pulses to ocular tissue at a plurality of target locations with a thermal relaxation time delay to limit the temperature rise of the targeted ocular tissue. There is no teaching in this patent application of the use of the system to target the optical disk.

U.S. Pat. No. 5,923,398 A has disclosed a more practical approach by introducing peripheral light therapy by interactive light field for non-visual stimulation, taking advantage of the fact that the peripheral retina is less engaged in conscious vision, thus less deteriorating the normal vision. However, despite its complex design, the device taught in this patent document does not exclude completely the stimulation of vision-forming receptors in the eye (rods and cons are still hit in off-axis photon stimulation).

A device and method for treating the visual system of a human being is known from U.S. Published Patent Application No. 2007/0182928 (Sabel, assigned to Novavision Inc.). The method includes the steps of locating and defining a blind zone of deteriorated vision with the human's visual system, defining a treatment area which is located predominantly within the blind zone and then treating the human's visual system by presenting visual stimuli to the human's visual system. The visual stimuli are presented on, for example, a computer screen. It will be noted that the term "blind zone" used in this patent application is not to be equated with the term "blind spot" or "optical disk" and the method does not include the selective application of light to a blind spot.

Finally, International Patent Application No. WO 2016/145064 A1 discloses systems and methods for controlling illumination relative to the circadian function of individuals using eyewear, but the patent document fails to teach a method to eliminate the interference of light therapy with the normal daily conscious vision.

SUMMARY OF THE INVENTION

This disclosure teaches an apparatus, a system and a method to stimulate the optic nerve. The apparatus comprises of one or more light emitting sources, an optical system to deliver and/or refract the light from the one or more light-emitting sources to an optic disc.

The system with the apparatus further comprises a processor for controlling a temporal and spatial pattern of the stimulation as well as the wavelength and intensity of the light based on a predefined or personalized algorithm and input from sensors which collect data from external parameters and/or physiological parameters, and an adjustable wearable frame for housing the system and calibration of the light rays to hit the retinal target area.

The method enables stimulation of intrinsically photosensitive retinal ganglion cells (ipRGCs) by directly shining light on the optic disk where the melanopsin-containing axons of ipRGCs converge.

The apparatus and method enable treatment with no pharmacological interventions/side effects, no interference with natural visual function of the eyes, invisible light stimulation, no harm to the image-forming areas of the retina, and no compromise to the attentional and perceptual performance of the user.

In one aspect of the disclosure a method for application of light to one or more eyes of a user is described. This method comprises the identification of location of an optic disk on a retina in the one or more eyes, and selectively applying the light onto the optic disc to stimulate the optic disk. The selective application of the light onto the optic disk enables strong light to stimulate the optic disk without damaging other parts of the retina.

The light is selected to have wavelengths in the range of 360 to 540 nm. In another aspect of the invention, the light is selected to have a wavelength in the range of 480+/−40 nm.

The identification comprises at least one of exposing the user to a stimulating light applied to the retina of the one or more eyes and monitoring perception of the stimulating light, or mapping of the retina.

There are various ways of producing the light. These include, but are not limited to, one of an LED source, a laser emitter and a display device.

The method can also comprise limiting a field of vision of at least one of the eyes. This is designed to ensure that the user is not distracted and moves her eyes, thus causing the light to impact on other parts of the retina.

The method may additional comprise monitoring at least one of a position of a pupil in the one or more eyes (300) or a direction of sight of the one or more eyes. This enables the light to be switched off if it is determined that the light is no longer directed towards the optic disk.

The method may also further comprise adapting composition of the light. This adaption is useful to adapt the light to the user.

The method has many applications, such as the treatment of myopia

The disclosure also teaches a device for implementing the method. The device comprises a light emitting source for emitting the light, an identifier for identifying location of an optic disk on a retina in the one or more eyes, and an optical system adapted to apply selectively the emitted light onto the optic disk. A controller may be provided for controlling the device. For example, the controller would adapt the optical system and/or the light composition.

The identifier could, for example, be a device for mapping the retina of the one or more eyes.

In an aspect of the disclosure, the device further comprises an eye tracking system, an electrooculography system or an electroretinography system for monitoring at least one of a position of a pupil in the one or more eyes, or a direction of sight of the one or more eyes.

The device may also comprise one or more mechanical or electro-optical actuators for changing a position of the light emitting source. These work in conjunction with the eye tracking system to ensure that the light is directed towards the optic disk. Similarly, the device may further provide that the optical system is adaptive to at least one of a position of a pupil in the one or more eyes or a direction of sight of one of the one or more eyes.

In a further aspect of the invention, the optical system may be additionally adapted to apply selectively the emitted light onto other parts of the eyes. This emitted light may have the same combination of light or a different combination of light than the light applied to the optic disk.

DESCRIPTION OF THE FIGURES

For a more complete understanding of the present invention and the advantages thereof, reference is now made to the following description and the accompanying drawings, in which.

DETAILED DESCRIPTION OF THE INVENTION

Figure 1:
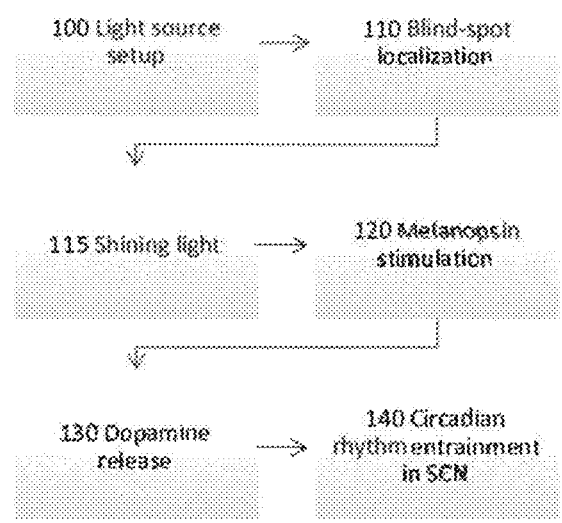
FIG. 1 shows an outline of the method of this disclosure.
Figure 2:
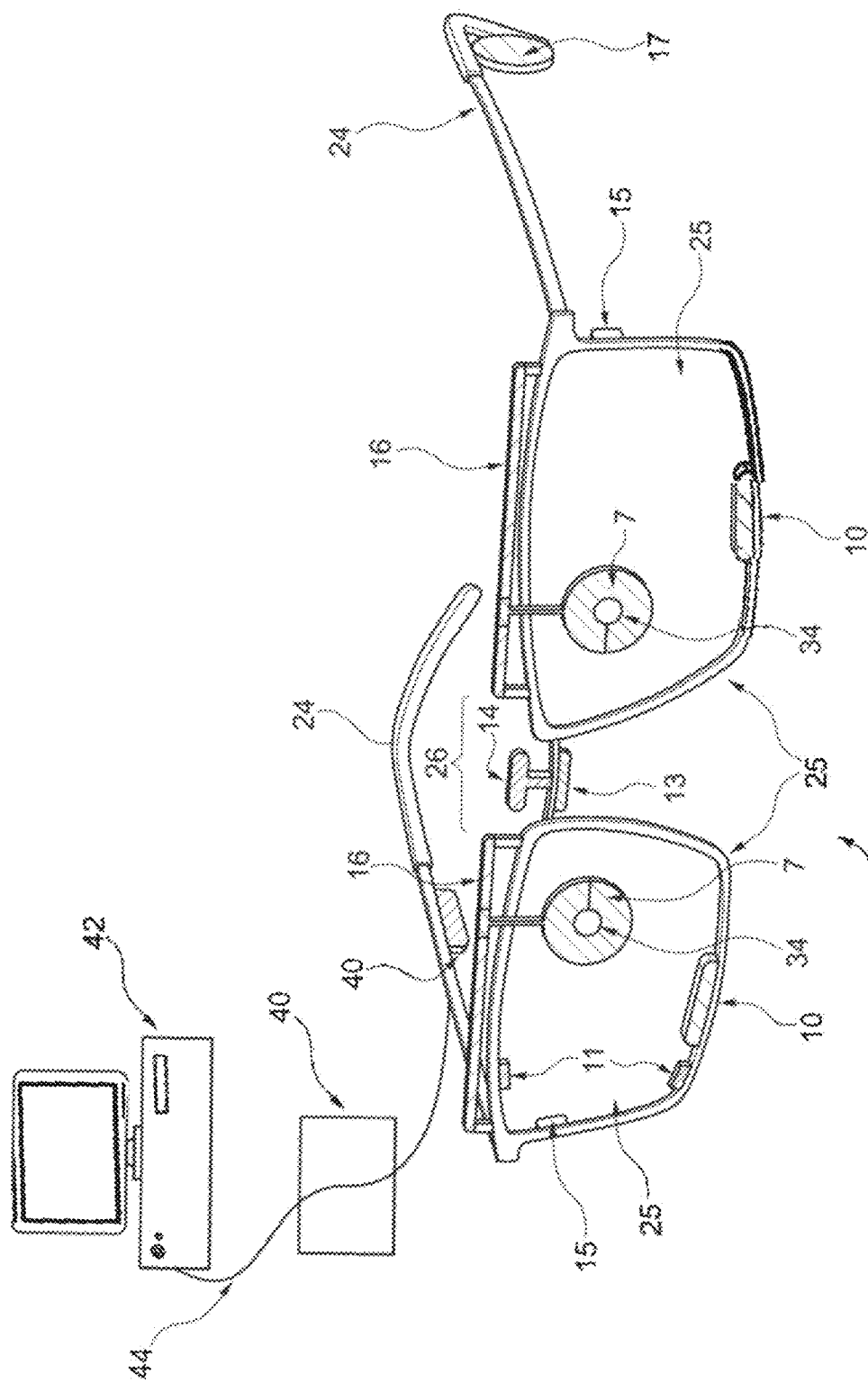
FIG. 2 shows an example of an apparatus used in this disclosure.

An outline of a method of light therapy by stimulating an optic nerve of a mammal, such as a human being, without impairing the normal vision is shown in FIG. 1. The apparatus and system used for implementing the method is shown in FIG. 2.

Figure 3:
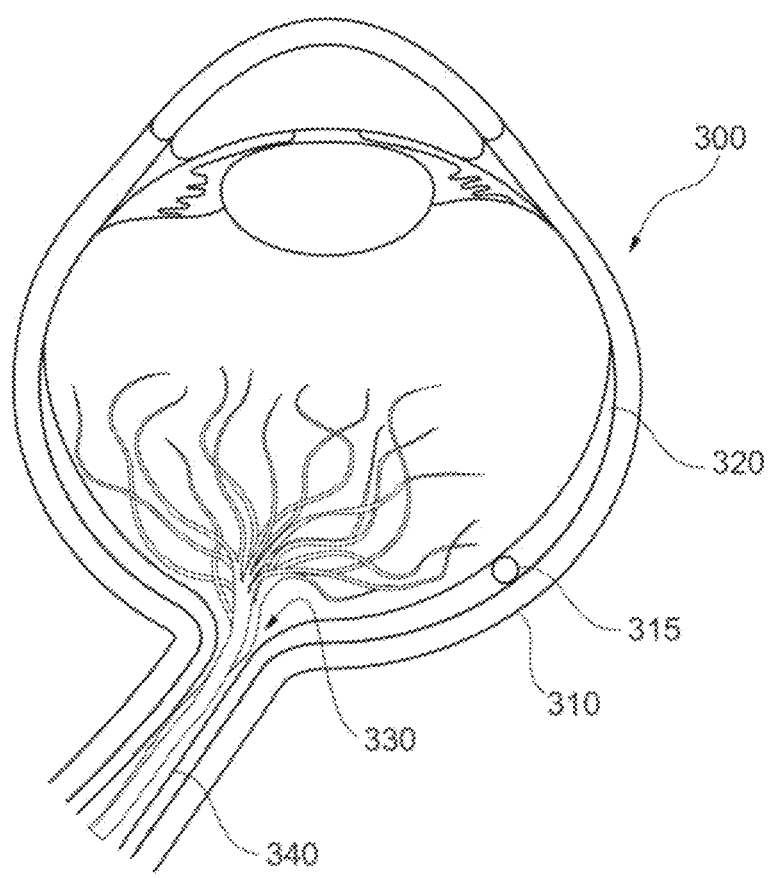
FIG. 3 shows an example of an eye.

FIG. 3 shows an example of an eye with the biological features of the eye 300 noted. The eye 300 has an eyeball 310 with a retina 320 in which a blind spot 330 or optic disc is situated. The retina 330 is connected to the optic nerve 340 which transfers signals formed on the retina 320 to the brain. The optic disc 330 is the raised disc on the retina 320 at the point of entry of the optic nerve 340, lacking visual receptors and so creating a blind spot.

At step 100, a light source is chosen and setup. The light source setup step 100 is the process of selection of the optimal wavelength, intensity, temporal and spatial pattern of a light stimulus via a controller device based on internal parameters of the body of the user or external parameters of the ambient. The light source setup step 100 can be the process of choosing a predefined set of parameters or individualized parameters, or selection of light properties depending on the ambient lighting, time, etc. The light source setup step 100 can be based on artificial intelligence algorithms or employ computational models of the eye 300 and/or the body.

In step 110 the blind spot of the eye is identified, for example, by shining light at the selected wavelength or another visible light wavelength onto the optic disc 330 in the eye 300. The aim of this step is to ensure an invisible delivery of light to the non-image forming parts of the retina 320 in the eye 300, i.e. the optic disc 330. Blind-spot localization is based on the geometrical properties of the eye and subjective report of the user. A closed-loop control of the invisible light therapy is done by an electrooculography system or pupil monitoring. The blind-spot localization can be an automatic, semi-automatic or manual procedure carried out by the device or by the user. In another aspect of the method, the optic disc 330 is identified by mapping the retina 320. This mapping can be done automatically or by an ophthalmologist.

Examples of systems that enable identification of the optic disc 330 by the mapping of the retina 320 include video-based imaging systems, eye-tracking systems, pupilometers, fundus imaging, retinoscope and ophthalmoscopes.

Light is shone onto the optic disk in step 115 and melanopsin stimulation is carried out in step 120. The axons of ipRGCs present at the optic disc are stimulated by light.

The ipRGCs are subset of retinal ganglion cells which exclusively express melanopsin, a photopigment for non-image forming visual functions such as circadian rhythm entrainment. The method aims to stimulate the optic-nerve-forming axons of all ipRGCs of retina on the optic disc. The stimulation of melanopsin expressing axons/ganglion cells stimulates the release of retinal dopamine in step 130. The release of dopamine by light entrains in step 140 the LD cycle by the Circadian rhythm master clock in the SCN in the brain.

FIG. 2 shows an example of an apparatus 1 used in this disclosure. It will be appreciated that the apparatus 1 shown is merely a non-limiting example. The apparatus 1 comprises essentially a pair of spectacles or eyeglasses comprising a spectacle frame 24, a bridge 26 and two lenses 25. The apparatus 1 is connected to a computer 42 and a controller 40 by a cable 44 (or through a wireless connection). The controller 40 could be mounted onto the spectacle frame 42 or could be a separate unit.

The lenses 25 have electrodes for an electrooculogram or electroretinography system. These are shown as vertical electrodes 11 on the left-hand lens 25 and horizontal electrodes 15 on both lenses 25 as well as a reference electrode 14 on the bridge 26. It will be appreciated that only one pair of vertical electrodes 11 are needed since the eyes 300 move in parallel. Element 13 represents a variety of sensors which are also mounted on the bridge 26. Theses sensors include, but are not limited to, ambient sensors, light sensors, time-of-flight camera (ToF), distance sensors, temperature sensors, cameras, etc.

The lenses 25 have an eye tracking system 10 mounted on them to establish the position of pupil and the direction of sight. Each of the lenses has a light emitting source 34, which could be for example an LED, a laser light or a projection/generation on a display. The light from the LED could be blue or another color or a mixture of colors. The mixture could be generated as a sequential RGB series of colors in rapid succession, or the mixture could be combined at the same time.

It is possible that the light emitting source 34 is separate from the eye glasses 1. Non-limiting examples of other light emitting sources 34 include digital light processing, laser beam steering, liquid crystal on silicon (LCoS), microscanner, virtual retinal display, an EyeTap device, micro or pico projectors, holography, or a light field. These light-emitting sources can be incorporated into a head-up display (HUD), an optical head-mounted display (OHMD) or even as implantable light sources insider the eyeball or on the optic disc.

An optical system 7 directs the light from the light emitting source 34 onto the optic disk 330 of the eye 300, as will be explained later. The optical system 7 comprises, for example, a wave guide and may include other elements. The optical system 7 is mounted on rails in this example on which motors run to move the position of the light emitting source 34, if required. It will be appreciated that the optical system 7 and the rails 16 enable the light from the light emitting source 34 to be directed within the eye 300 and adjusted easily for different users. Further examples of the optical system 7 include, but are not limited to diffractive devices, prisms, holographic devices, polarizing devices, beam-splitting devices, clear-vu devices, switchable devices, or mirror devices. Mirror devices include pin mirrors or one-sided mirrors. It would be also possible to use combined devices, such as a birdbath device having a beam splitter with an optical combiner.

A body sensor 17 is also attached to the spectacle frame 24. The role of the body sensor 17 is to measure parameters relating to the temperature, heart rate and other physical parameters of the user. The information is communicated to the controller 40 and processed.

A recent study showed that the light projected inside the blind spot 330 of the human eye 300 enhances pupillary light response (Miyamoto and Mirakami, "Pupillary light reflex to light insider of the natural blind spot", Scientific Reports, 5:11862, DOI: 20.1038/srep11862, June 2015) which evidenced the presence of photopigment melanopsin on the optic disc 330, where no other visual photoreceptors exist. It is known that the ipRGCs connections to the olivary pretectal nucleus mediate light-sensitive pupil constriction (Dijk and Archer, "Light, Sleep and Circadian Rhythms: Together Again", PLOS Biology, Vo17, issue 6, e1000145, June 2009).

There are no image-forming receptors on the optic disc 330. Thus the projection of the light on the optic disc 330 does not lead to impairment of the normal vision, glare or dazzling, and overt and covert attentional and perceptual impairments of the visual processing.

The projection of the light onto the optic disc 330 does not lead to undesired pupil constriction, because stimulating the optic disc 330 only is not enough to trigger pupil constriction (Miyamoto & Murakami, 2015).

On the other hand, conventional whole-eye light therapy over the whole eye 300, not just limited to projection of light onto the optic disk 330, leads to stimulation of photoreceptors in the retina 320 non-selectively. This conventional whole-eye light therapy leads to unknown effects on the inter-retinal circuits and/or higher cortical processes via image-forming pathways, which may cause conscious information processing impairments and/or mental or affective side effects e.g. sleep disorders, stress, depression, or anxiety, as well as malfunctions of the brain such as seizure, epilepsy, etc.

Several stimulation parameters should be taken into account when using light therapy on a patient for performing an optimal light treatment. These stimulation parameters include, but are not limited to, temporal pattern of the light, spatial pattern of the light, intensity, duration, wavelength of the light etc. It is known that intensity, wavelength, spatial properties and temporal pattern of the light stimulation in previously described methods have to be adjusted in order to reduce the perception of the light treatment by the patient. This is discussed, for example, in international patent application WO 2016162554 A1.

The method of this disclosure enables any intensity and duration of light to be deliverable to the eyes 300 of the patient, since there is no visual photoreceptors on the optic disc 330 to be harmed. Moreover, the response profile of ipRGCs are different from other types of photoreceptors in the retina 330 (i.e. rods and cons). Temporal structure of the stimulating light (frequency of the flicker, on/off pattern etc.) can be optimized for the ipRGCs with regards to the needs of the patient. This change is independent of the response profile of the other photoreceptors, because ipRGCs are the only photoreceptors on the optic disc 330 and no light is shone on the other parts of the retina 320.

The stimulation parameters described previously can be adjusted independently of each other to keep the total parameter intensity below a certain threshold which prevents light scattering from the optic disc 330 to other regions of the retina 320 in the eye 300. These other regions contain image-forming photopigments and cause visual perception of the stimulating light.

Melanopsin receptors on the optic disc 330 are found to be optimally sensitive to the sharp blue light wavelength. Thus using light of this wavelength should provide an efficient phototherapy treatment. There is less of a safety issue using the blue light wavelength than with conventional light therapy, such as blue light hazard, as the delivery of the light is not via the retina i.e. rods and cons. There are no rods and cons on the optic disc 330, as previously noted. The blue light, which is part of the visible light spectrum, reaches deeper into the eye 300 during conventional whole-eye stimulation and its cumulative effect can cause damage to the retina 320. Furthermore, in certain wavelengths, the blue light is implicated in the development of age-related macular degeneration (AMD).

The method could be applied to a daily routine of a normal life. As described in the preferred embodiments, the emitting source 34 which selectively emits light to the optic disc 330 can be housed in the spectacle frame 24, or can be added on the current spectacle frame 24 of the patient. No additional complex eye wear like a virtual reality device, such as but not limited to Google glass Microsoft HoloLens, Magic Leap, Intel Vaunt or Oculus Rift, is needed to perform this method. Therefore, the normal visual function of the eye 300 is not impaired and the natural foveal eye sight is preserved. Advantageously, stimulation can also be applied during night with no sensation of the light for the subject, which makes the method applicable to people who need light therapy during dark times without exposing them to visual light.

The method requires no optical or chromatic filter (as proposed in the international patent application WO 2016162554 A1) to filter the visible spectrum, because there is no image-forming photoreceptor on the optic disc 330. Moreover, there is no spatial adjustment/control required during the light therapy (as taught in the international patent application WO 2016/162554 A1) to change the spatial structure of stimulus to keep the stimulation less disturbing, since the position of the optical disc 330 on the retina 320 is constant and the stimulation remains invisible. Methods are provided to keep the emitted light within the optical disk 330 relative to the gaze direction.

The spatial density of ipRGCs (only 1 to 3% of retinal ganglion cells) is much lower that com that of rod photoreceptors. The probability of absorbing a photon by the ipRGCs is more than 1 million times lower for a given retinal area of photostimulation. Thus, some prior art methods with a whole retinal stimulation approach assume that the ipRGCs receive additional input from a complementary photoreception process involving rods. Other known methods involve both the direct stimulation of ipRGCs by extending the transmitted spectral range to 460-520 nm and the indirect stimulation by the incoming rod driven signals peaking near 500 nm. However, these prior art methods have the disadvantage that the light will be visible via rods photoreception. The method discussed in this document specifically stimulates all of the ipRGCs on the converging point of the axons of all retinal ganglion cell (RGCs)s on the optic disc 330 in the absence of any other kind of receptors.

Melanopsin is the main photoreceptor in the retina 320 which regulates the circadian rhythm. The method of this disclosure targets the melanopsin, which is expressed on the axons of ipRGCs on the optic disc 330, among other places. The RGCs which express other types of photoreceptor proteins (e.g. rhodopsin) are not necessary for the circadian system (as is evidenced in blind people). Stimulating non-melanopsin expressing RGCs may provide indirect input to the circadian master clock. The stimulation of the optic disc 330 provides the highest specificity in targeting the melanopsin which gives the highest degree of freedom to the system to adjust least number of the stimulation parameters described previously for an optimal non-visual forming stimulation.

The stimulated optic nerve 340 directly sends the light signal to the SCN via the RHT, the highway to the circadian master clock center in the brain. In other words, the system provides ocular (but not visual) stimulation instead of less specific channels like ear canal stimulation or through other extracranial positions (as disclosed, for example in WO 2015010920 A1).

The optic disk 330 stimulation is via one or an arrangement of light emitting diodes (LEDs) or similar in the emitting source 34, which is housed in the spectacle frame 24. This enables a precise control of the direction of the light to the eye 300 by the optical system, such as an optical guide tube. The optical guide tube ensures an exclusive delivery of light to the optic disc 330 on the retina 320.

In another aspect, the stimulation pattern is provided in a gaze-contingent manner to the eye by a change in the wavelength, luminance, and other parameters of the display (e.g. TV, monitor, screens, virtual reality (VR) goggles (including light-field technology in which enables light from a display to hit multiple focal planes in the eye), augmented reality (AR) goggles, mixed reality (MR) goggles, beamer, internet of things (IoT) devices, smart home appliances, smart lighting systems, interior design arrangements, car internal displays or windshield etc.) on the regions of the display which correspond to the blind spot. The gaze direction is measured online with an eye tracking system (remote or mobile) and the spatial location of the stimulation pattern changes according to the position of the eye 300. The stimulation pattern may be optimized to deliver particular wavelengths with specific temporal and spatial pattern. The pattern does not impinge on the holistic perception of the visual input from the display, since the perceptual filling-in process of the visual system interpolates the absence of visual input falling on the optic disk 330. Such an embodiment is ideal for applications where the patient spends working hours in front of a computer monitor or is watching TV, etc.

In another aspect, the light emitting source 34 is combined with a strong myopia control lens as the lens 25 on the spectacle frame 24. A myopia control lens is a powerful tool to control myopia. The myopia control lens provides large positive correction in the periphery while keeping the central vision clear. The strong blur in peripheral vision helps the patient to keep the eyes 300 in the center (like pinhole) which consequently limits the gaze dynamics and helps the light stimulation remained within the optic disk 330.

In another aspect, the optical guide tube is a pinhole which guides the light from the LED in the light emitting source 34 on the spectacle frame 24 to hit the optic disc 330. The optic disc 330 in human eye 300 corresponds to the blind-spot with a relatively large size of 5-7 visual degrees at an angle about 15 visual degrees lateral to the fovea 315. In this embodiment, the gaze dynamics is limited and a pinhole ensures that the light therapy remains invisible inside the blind spot. For such an embodiment, the user must use the spectacle frame in routine static scenarios, like working in front of a monitor or watching TV. Excessive eye movements are restricted naturally, since the pinhole does not allow for peripheral view, so the gaze movements translate to a head movement, when necessary. The position of the optic disk 330 remains constant relative to the light emitting source 34 while a head of the user moves instead of the eyes 300.

The light can be polarized and emitted through a polarized filter on the spectacle lens 25. This ensures that the light always reaches the eye 300 perpendicularly. The light does not reach the retinal photoreceptors beyond the optic disk 330 if the light emitting source 34 is positioned and calibrated according to the position of the eye's 300 in the patient and the position of the spectacle frame 24 relative to the position of the optic disk 330.

In another aspect, the electrooculogram (EOG) or the electroretinograph electrodes are housed in the spectacle frame 24 and temples, as discussed above. The EOG signals the gaze direction and enables automatic on/off switching of the light emitting source 34 according to the position of the eye 300. When the eye is looking straight relative to the light emitting source 34, the stimulation pattern falls on the optic disk 330. When the eye 300 is looking off-center, the pattern switches off, in order to not fall on the other light sensitive parts of retina 320 (see also US 20040070729 A1).

The control system of the light switch and the EOG system takes into consideration the necessary temporal characteristics of the stimulation as well as frequency limits of the EOG system to ensure a precise switching time of the light emitting source 34 such that the subject does not see the light at any time.

The light emitting source 34 is advantageously housed in the form of the spectacles 20. A one-time calibration procedure allows the correct positioning of the light emitting source 34 in order to stimulate the optic disk 330. The calibration comprises a subjective guide of the patient to make a test light invisible to the patient by spatially aligning its position and size on the optic disk 330. In another calibration procedure, an eye tracking system together with a 3D model of the eye 300, guides the first installation of the light emitting source 34 on the spectacle frame 24 for the wearer by measuring the gaze direction and the relative position of the optical disk 330 to the foveal fixation. In either calibration procedures, the relative position of the light emitting sources 34 to the center of each eye 300 is adjustable on a freely moving rail system installed on the spectacle frame 24.

In another embodiment, the light emitting source 34 can adaptively change position and/or direction according to the eye position and gaze direction. In this scenario, the light can be continuously shone to the eye 300 and always remain inside the optic disk 330. This is useful for continuous emission mode for longer exposure times.

A controller is configured so as to provide a personalized light therapy for the patient with, for example, a specific emitted wavelength in front of the eye 300. Thus the pattern of the stimulation light can be changed for example for epileptic patients. The controller can parametrically change the temporal pattern, intensity, wavelength, spatial pattern, duration of the light etc. The controller can control the stimulation pattern according to external parameters such as environmental light level, time, etc. It can control the stimulation pattern according to internal parameters such as physiological factors, heart rate, temperature, pupil size, eye lid position, etc. It can control the stimulation pattern according to personalized information such as age, size, gender, etc. The controller is housed in the body and temple of the spectacle frame 24.

It is known that there is also melanopsin signaling in the iris as well as in the retina (Xue et al, Melanopsin signaling in mammalian iris and retina", Nature, vol. 479, 67-73, 3

Nov. 2011, DOI:10.1038/nature10567). The method and device of this document enables identifying the position of the pupil, and subsequently also the iris. It is therefore possible to stimulate the iris with the similar or different composition of light as well as stimulating the optic disc. The stimulation of the iris will also remain invisible as there is no image-forming photoreceptor on the iris.

In a further aspect of the method and system, it is also possible to shine light on other parts of retina if needed in conjunction with the stimulation of the optic disc. It has been shown that melanopsin receptors express a bistable behavior (Mure et al., "Melanopsin Bistability: A Fly's Eye Technology in the Human Retina", POS One, vol. 4, issue 4, e5991, June 2009). Shining a red light to the retina may therefore enhance the response of melanopsin receptors to blue light. It is also thought that sub-visible intensities of violet and ultra-violet light shone to the retina may have desired effects as explained in example applications of the device described in this document such as myopia.

EXAMPLES

Myopia

The method and system may be used in myopia prevention and/or reduction. It is known that myopia occurs when the eyeball 310 is too long, relative to the focusing power of the cornea and lens of the eye 300. This additional length of the eyeball 310 causes light rays to focus at a point in front of the retina 320, rather than directly on the surface of the retina 320. An adapted light therapy reduces the risk of myopia onset by acting positively on the production cycle of dopamine. Dopamine is a retinal neurotransmitter associated with light adaptation. Dopamine has an impact on the eye length and thus on myopia. Recent research shows that dopaminergic cells are linked to intrinsically photosensitive retinal ganglion cells and that they are regulated by the chronobiologic blue light at around 480 nm. This specific light is thought activate endogenous dopamine production, while a lack of this light (spectrum and/or light level) may inhibit dopamine production. The inhibition may in the long term contribute to the elongation of the eye. For further information see Myopia, light and circadian rhythms (Phillips et al, "Myopia, Light and Circadian Rhythms", Advances in Ophthalmology, Edited by Rumelt, March 2012) See also CN 1432348 A.

It has been shown that a broken LD cycle can lead to myopic eyes. It is prevalent in cities where children do not get outside enough and experience natural sunlight. A recent study showed that violet light (360-400 nm wavelength) suppresses myopia progression (see Torii et al, "Violet Light Exposure Can Be a Preventive Strategy Against Myopia Progression", EBioMedecine, 15 (2017) 210-219) also the patent application PCT/JP2015/065997 for a myopia prevention device). This part of the light spectrum is usually excluded from our industrialized world due to the use of UV protection. Short wavelength light exposure, however, has been a topic of research for decades and has been shown to induce photo-oxidation and retinal degeneration (Schaeffel and Smith, "Inhibiting Myopia by (nearly) invisible light", EBioMedecine, 16 (2017) 27-28, DOI: 10.1016/j.ebiom.2017.01.016). Therefore, short wavelengths stimulation of the optic disk 330 is advantageous regarding safety concerns, because the light does not hit the retina 320 but only the optic disk 330 which has no rods and cons.

Long wavelength light (650 nm, red), on the other hand, has been shown to act as a strong inhibitor of eye growth in rhesus monkeys and tree shrews, while the opposite was found in chickens. Other wavelengths studies in the myopia research include bright blue-green light which is largely involved in the endogenous production and regulation of melatonin.

Further studies have indicated that under natural conditions, green light in the evening and early biological nighttime may be as effective or, in some scenarios, more effective than blue light and that the relative effectiveness of green light decreases across a night, such that blue light is relatively more effective than green light for influencing circadian responses in the late night and early morning hours. Therefore, the timing of stimulation is relevant in addition to the stimulation wavelength. The method and apparatus in this disclosure enable an independent adjustment of the light wavelength, as well as intensity, duration, and precise timing of stimulation according to the endogenous and exogenous biological rhythms. Moreover, light that flickers (as opposed to being constant) can be even better for dopamine production. The current method and system has no constraints in regards with the temporal pattern of the stimulation.

Combining blind-spot light therapy with filtering of the light reaching retina (e.g. red light filtering) is also possible to minimize or prevent from progressive myopia.

There is also evidence that dopamine produced elsewhere than in the retina 320 can have an effect on myopia prevention. L-Dopa is a drug which increases dopamine concentrations, and this drug has been shown to inhibit myopic shifts occurring when the patient is deprived of light. This indicates that an increase in dopamine levels can inhibit the progression of myopia regardless of whether the dopamine is produced via light stimulation through the eye 300. Thus light stimulation of the optic disc 330 to produce the dopamine can have a similarly positive effect on myopia as L-Dopa, but without pharmacological interventions side effects.

Researchers recommend two to three hours outside every day. On the other hand, light can be bad for myopia if presented at the wrong time (out of sync with circadian rhythms). A problem may occur where children need dopamine-enhancing light treatment to help prevent myopia, but they cannot be relied upon to action the treatment at the right times or, conversely, to not action treatment at bad times. The method and apparatus allows invisible light therapy through the eyes anywhere anytime, while the patient does not need to take control of the stimulation and/or timing.

Sleep

Under normal conditions, there is a stable phase relationship among circadian rhythmicity, sleep, and the light-dark cycle. In animals living under natural conditions, uncoupling of sleep and circadian rhythmicity from their normal phase, relative to the entraining light-dark cycle rarely, if ever, occurs. However, humans routinely disrupt the normal synchronization of the sleep-wake and light-dark cycles, either for short periods of time (i.e., following rapid travel across time zones, referred to as the "jet lag" syndrome), or for long periods of time (i.e., as occurs in "shift workers"). The impact of light on human non-image forming responses is dependent upon the correlated color temperature (CCT) of the light, rather than the type of light itself (e.g., incandescent, fluorescent, LED, etc.). Preventing circadian disruption and melatonin suppression may require substantial alterations of the CCT of the light night shift workers are exposed to. Although effective for protecting melatonin and other circadian rhythms, the practical utility of these methods may be limited as the complete absence of short wavelength light may lead to reduced contrast and acuity which presents safety concerns for some night workers or surgeons, among other deficiencies. The method and apparatus can be used as an alternative to such changes to entrain the circadian rhythm to its natural cycle. Potential applications include use by the shift workers, the travelers, individuals exposed to light from artificial light sources during a time of circadian night relative to their circadian rhythms, individuals seeking to normalize their circadian rhythm, etc.

In addition to influencing the perception of visual images, light coordinates the temporal rhythms of physiology and behavior by sending signals to structures in the brain that contain the central circadian clock. These signals are mediated in part by melanopsin, a photopigment found in the retina. Light affects the brain through these nonvisual pathways, and scientists have recently begun to realize just how pervasive these nonvisual effects are. Mounting evidence supports the view that the effects of light on sleep and brain activity during wakefulness, as well as the duration of sleep and the homeostatic response to sleep loss, depend on both melanopsin and circadian time (Dijk & Archer, 2009). The present method and apparatus can be used for sleep disorders and/or jet lag problems or improving shift workers' well-being, by stimulating, the dopamine release and melatonin regulation through optic disc light therapy.

Other Applications

The method and apparatus of this document may be used in therapy for treatment of patients suffering from chronobiologic disorders such as circadian rhythm sleep disorders, sleep disorders, pupil dilation, delayed and advanced sleep phase syndromes, mood disorders, seasonal affective disorder such as depression or fatigue, postpartum depression, cancer risks, hormonal disorders, alertness disorders and cognitive performances, appetite and obesity, memory disorders, psychomotor disorders, body temperature deregulation, premenstrual disorders, epilepsy crisis. The apparatus and the method can be employed to achieve increased levels of human alertness and performance e.g. in working environments. The system and the method can be used to treat various other disorders such as migraines, anxiety, Obsessive Compulsive Disorder (OCD), and alcohol and nicotine addiction.

The method and system according to the invention can compensate inadequate lighting conditions (lack of beneficial blue at specific moments) to help the biological clock to remain synchronized through the good blue/melatonin secretion relationship. Circadian rhythms may be observed in various physiological functions including, but not limited to, sleep/wake cycle, feeding times, mood, alertness, cognitive function, cell proliferation and gene expression in various tissue types. Various tissues and cell types contain independently oscillating cellular clocks, such as the liver, kidney and pancreas, among others, and can function autonomously through circadian expression of their "clock genes", although they are normally modulated and synchronized by the central SCN clock.

Light therapy essentially adjusts the amount of the melatonin in the body. Evidence of oncostatic effects of melatonin that have been shown in vitro, and in animal studies, suggest a key role in suppressing tumors and protecting against the proliferation of cancer cells, including human breast and prostate cancer, Low levels of nocturnal melatonin release may be associated with breast cancer, prostate cancer, type 2 diabetes, metabolic syndrome, insulin resistance, diabetic retinopathy, macular degeneration, hypertension, coronary artery disease, congestive heart failure, depression, anxiety, migraines and other life threatening or debilitating conditions. In recent years, there has been an increasing recognition that melatonin may confer protection from disease, and lower levels of melatonin have been associated with a wide variety of diseases and chronic conditions. The scope of this relationship may be potentially far-reaching, and may include cancers, cardiovascular disorders such as hypertension and coronary artery disease, metabolic disorders such as insulin resistance and type II diabetes, Huntington's disease, multiple sclerosis, Alzheimer's disease, migraine headaches, and psychiatric disorders such as depression and anxiety, etc. In some diseases, such as cancer, there appears to be an inverse linear relationship between melatonin levels and disease risk, such that lower melatonin levels are associated with a significant increase in disease risk. Furthermore, there is no clear "threshold" for this relationship, suggesting that any loss of endogenous melatonin due to light exposure at night would be associated with relatively increased disease risk. For this reason, there may be a need to minimize circadian disruption, and protect neuroendocrine rhythms such as melatonin.

A device according to the method disclosed by the invention may be also used in therapy for treatment of subjects suffering from epilepsy. Recent research suggests that some forms of epilepsy and depression are bidirectional conditions, which suggests that light therapy could be an effective treatment for some people with epilepsy. Endogenous melatonin production seems to have an influence on seizure thresholds for patients with temporal lobe epilepsy. Besides, bright blue-green light is largely involved in the endogenous production and regulation of melatonin. Thus, we can hypothesize that bright blue-green light is involved to some extent in modulation of seizure thresholds. For people suffering from lobe temporal epilepsy, light may help smooth out some of the seasonal peaks in seizure frequencies.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

REFERENCE NUMERALS

1 Apparatus
7 Optical system
10 Eye tracking system
11 Vertical electrodes
13 Sensors
14 Reference electrode
15 Horizontal electrodes
16 Rails
17 Body Sensor
Spectacle Frame
25 Lenses
26 Bridge
34 Light Emitting source
40 Controller
42 Computer
44 Cable 300 Eye
310 Eyeball
315 Fovea
320 Retina
330 Blind Spot or Optic Disk
340 Optic nerve

What is claimed is:

1. A method for invisible targeting with light of melanopsin in one or more eyes of a user, comprising:
    identification of a location of an optic disk on a retina in the one or more eyes; and
    positioning a light emitting source to spatially align a position and size of the light on the optic disk to make the emitted light invisible to the user; and
    selectively applying the light, configured to stimulate melanopsin, onto the optic disc to invisibly target and stimulate the melanopsin located at the optic disk to inhibit a progression of myopia of the user.

2. The method of claim 1, wherein the light is selected to have wavelengths in a range of 360 to 540 nm.

3. The method of claim 1, wherein the identification comprises at least one of exposing the user to a stimulating light applied on the retina of the one or more eyes and monitoring perception of the stimulating light, or mapping of the retina.

4. The method of claim 1, wherein the light is emitted from one of an LED source, a laser emitter or a display device.

5. The method of claim 1, further comprising limiting a field of vision of at least one of the eyes.

6. The method of claim 1, further comprising monitoring at least one of a position of a pupil in the one or more eyes or a direction of sight of the one or more eyes.

7. The method of claim 6, further comprising changing composition of the light.

8. The method of claim 1, further comprising selectively applying the light onto other parts of the one or more eyes.

9. A method for a treatment of myopia of a user by invisible targeting with light of melanopsin in one or more eyes of the user, the method comprising:
    identification of location of an optic disk in a retina in one or more eyes; and
    positioning a light emitting source to spatially align a position and size of the light on the optic disk to make the emitted light invisible to the user; and
    selectively applying the light, configured to stimulate melanopsin, onto the optic disc to invisibly target and stimulate the melanopsin located at the optic disc to inhibit a progression of myopia of the user.

10. A device for invisible targeting with light of melanopsin in one or more eyes of a user, comprising:
    a controller for selecting light configured to stimulate melanopsin;
    a light emitting source for emitting the light;
    an identifier for identifying a location of an optic disk on a retina in the one or more eyes, and an optical system adapted to selectively apply the emitted light, configured to stimulate melanopsin, onto the optic disk, by positioning the light emitting source to spatially align a position and size of the light on the optic disk to make the emitted light invisible to the user and thereby stimulating the melanopsin located at the optic disk to inhibit a progression of myopia of the user.

11. The device of claim 10, further comprising a field of view limitation device.

12. The device of claim 10, wherein the controller is configured to select the light to have a wavelength in a range of 360 to 540 nm.

13. The device of claim 10, wherein the identifier comprises a device for mapping the retina of the one or more eyes.

14. The device of claim 10, wherein the light emitting source is one of an LED source, a laser emitter or a display device.

15. The device of claim 10, further comprising an eye tracking system or an electrography system for monitoring at least one of a position of a pupil in the one or more eyes or a direction of sight of the one or more eyes.

16. The device of claim 15, wherein the light emitting source is adapted to change composition of the light.

17. The device of claim 10, wherein the optical system further additionally applies the emitted light on to other parts of the one or more eyes.

18. The device of claim 10, further comprising one or more actuators for changing a position of the light emitting source.

19. The device of claim 10, wherein the optical system is adaptive to at least one of a position of a pupil in the one or more eyes or a direction of sight of one of the one or more eyes.

20. The method of claim 1, further comprising
    measuring at least one of external parameters and internal parameters, wherein the external parameters include an environmental light level, time-of-flight, and daytime, and wherein the internal parameters include physiological factors, heart rate, temperature, pupil size, eye lid position, age, size, and gender of the user;
    wherein the selecting of the light configured to stimulate melanopsin is based on at least one of the measured parameters and predefined parameters.

* * * * *